(12) United States Patent
Sawant

(10) Patent No.: US 8,481,591 B2
(45) Date of Patent: Jul. 9, 2013

(54) POLYMERIC TOPICAL COMPOSITIONS

(75) Inventor: Prashant Sawant, Rowville (AU)

(73) Assignee: Stiefel Research Australia Pty. Ltd., Rowville, Victoria (AU)

( * ) Notice: Subject to any disclaimer, the term of this patent is extended or adjusted under 35 U.S.C. 154(b) by 177 days.

(21) Appl. No.: 12/916,692

(22) Filed: Nov. 1, 2010

(65) Prior Publication Data

US 2012/0108527 A1 May 3, 2012

(51) Int. Cl.
*A01N 43/16* (2006.01)
*A61K 31/35* (2006.01)
*A01N 43/04* (2006.01)
*A61K 31/70* (2006.01)

(52) U.S. Cl.
USPC ........................................................ 514/460

(58) Field of Classification Search
None
See application file for complete search history.

(56) References Cited

U.S. PATENT DOCUMENTS

| | | | |
|---|---|---|---|
| 4,393,076 A | 7/1983 | Noda et al. | |
| 4,675,009 A | 6/1987 | Hymes et al. | |
| 4,935,241 A | 6/1990 | Saitoh et al. | |
| 4,938,964 A | 7/1990 | Sakai et al. | |
| 4,940,579 A | 7/1990 | Randen | |
| 4,954,332 A | 9/1990 | Bissett et al. | |
| 5,081,157 A | 1/1992 | Pomerantz | |
| 5,082,656 A | 1/1992 | Hui et al. | |
| 5,304,368 A | 4/1994 | Shernov et al. | |
| 5,436,241 A | 7/1995 | Shin et al. | |
| 5,573,759 A | 11/1996 | Blank | |
| 5,658,559 A * | 8/1997 | Smith ........................ | 424/78.02 |
| 5,674,912 A | 10/1997 | Martin | |
| 6,010,716 A | 1/2000 | Saunal et al. | |
| 6,017,520 A | 1/2000 | Synodis et al. | |
| 6,123,924 A * | 9/2000 | Mistry et al. ................... | 424/45 |
| 6,211,250 B1 | 4/2001 | Tomlinson et al. | |
| 6,582,683 B2 | 6/2003 | Jezior | |
| 7,678,366 B2 | 3/2010 | Friedman et al. | |
| 2005/0175641 A1 | 8/2005 | Deo et al. | |
| 2007/0196323 A1 | 8/2007 | Zhang et al. | |
| 2007/0196325 A1 * | 8/2007 | Zhang et al. ............... | 424/78.07 |
| 2007/0219171 A1 * | 9/2007 | Lulla et al. .................... | 514/177 |
| 2008/0152603 A1 * | 6/2008 | Rudolph et al. ................ | 424/59 |
| 2008/0175810 A1 * | 7/2008 | Zhang ........................ | 424/78.05 |

FOREIGN PATENT DOCUMENTS

| | | |
|---|---|---|
| CA | 1300515 | 5/1992 |
| EP | 0212959 B1 | 3/1993 |
| EP | 0 944 398 B1 | 4/2004 |
| WO | WO 88/09185 A1 | 12/1988 |
| WO | WO 93/24105 A1 | 12/1993 |
| WO | WO 95/30409 A1 | 11/1995 |
| WO | WO 99/49835 A1 | 10/1999 |
| WO | WO 02/43739 A2 | 6/2002 |
| WO | WO 2008/094910 A2 | 8/2008 |

OTHER PUBLICATIONS

Dictionary definition of "alcohol," downloaded from the internet Nov. 2, 2012.*
"Dermacryl 79 for Skin Care Formulations", Personal Care Polymers, Specialty Products from Natl. Starch & Chem. Company, 1994, pp. 1-7.
Sawant et al., P., International J of Pharmaceutics 396, p. 45-52 (2010).
Sawant et al., Effect of Polymer Chemistry and Lipophilicity of Drugs on Drug Release, Presentation 11th Pacific Polymer Conference Dec. 6-11, 2009.
Sawant et al., Abstract for 11th Pacific Polymer Conference Dec. 6-11, 2009.

* cited by examiner

*Primary Examiner* — Layla Bland
(74) *Attorney, Agent, or Firm* — Dara L. Dinner; Theodore Furman

(57) ABSTRACT

The present invention relates to topical antibacterial compositions. The compositions comprise an antibacterial agent such as mupirocin, water, a polymer and a volatile solvent present in an amount of less than about 40%. The invention also relates to methods of treatment by administering the compositions to a patient in need thereof, and to the use of such compositions in the treatment of bacterial conditions.

29 Claims, 4 Drawing Sheets

(A)

(B)

(C)

POLYMERIC TOPICAL COMPOSITIONS

FIELD OF THE INVENTION

The present invention relates to topical antibacterial compositions.

BACKGROUND OF THE INVENTION

Bactroban® (2% mupirocin) ointment and Bactroban® (2% calcium mupirocin) cream and ointment are marketed by GlaxoSmithKline for the treatment of furuncle, impetigo and wounds that have become infected.

U.S. Pat. No. 5,082,656 (Hui et al.) describes an antibacterial composition for topical administration comprising: from about 0.5% to about 10% of an antibacterial compound, from about 1% to about 30% of a non water soluble polymeric composition, from about 0.5% to about 40% of a plasticizer, and from about 50% to about 95% of a solvent (such as ethanol or isopropanol). Upon topical application of the antibacterial composition, the solvent will evaporate and leave a thin protective film of polymeric composition which retains the antibacterial compound against the skin.

U.S. Pat. No. 6,211,250 (Tomlinson et al.) describes topical compositions comprising at least one rate modulating polymer, a volatile solvent and at least one physiologically active agent. Tomlinson discloses compositions comprising a hydrophilic polymer and a hydrophobic polymer selected to modulate the rate of release of the active agent. The compositions comprise greater than 50% volatile solvent. A high level of volatile solvent is desirable in as much as it will solubilize the hydrophobic polymer and evaporate to leave a polymeric film on the surface of the skin. However, a high level of volatile solvent has the potential disadvantage of irritating the skin, particularly on open wounds or lesions.

U.S. Pat. No. 6,582,683 (Jezior) describes a dermal barrier composition which comprises water, a hydrophilic polymer emulsion and a hydrophobic polymer emulsion. The dermal barrier composition is moisture activated, and remains inert until the hydrophobic and hydrophilic polymer emulsions contact a suitable substrate such as human skin. The dermal barrier composition is itself an emulsion, and may contain a biocidal agent for treatment of a skin disorder or condition. The dermal barrier composition may also contain other active agents such as sunscreens, insect repellents and fungicides. The composition does not contain a volatile solvent.

US Published Application No. 2005/0175641 (Deo et al.) describes topical compositions comprising at least one physiologically active agent, a volatile solvent, and ethyl cellulose as a hydrophobic polymer, along with a hydrophilic polymer. The volatile solvent is present in an amount of greater than 50% by weight.

U.S. Pat. No. 7,678,366 (Friedman et al.) describes a therapeutic nail varnish comprising a pharmaceutically active agent, a humectant, water, less than about 7.5% by weight of a polymeric film forming agent, at least one additional excipient, and a solvent system including at least one volatile solvent. Friedman et al. discloses pharmaceutically active agents which are antifungal agents, such as naftifine or terbinafine. The nail varnish may further comprise a second active ingredient, such as clobetasol.

There remains a need in the art for topical preparations that are able to deliver an active agent, particularly an antibacterial, to the surface of the skin in a controlled manner and without irritation. Furthermore, it is desirable that such a preparation would be cosmetically elegant, and rapidly dry after topical application to leave a film on the surface of the skin. The present invention is believed to address these unmet needs.

SUMMARY OF THE INVENTION

According to an embodiment, the present invention provides a topical pharmaceutical composition comprising an antibacterial agent, a polymer, water and less than about 40% volatile solvent.

According to another embodiment the present invention provides for a method of treating a disease, disorder or condition of the skin, in a mammal in need thereof, the method comprises administering to said mammal, preferably a human subject, a topical pharmaceutical composition comprising an antibacterial agent, a polymer, water and less than about 40% volatile solvent.

According to a further embodiment, the invention relates to the use of a topical pharmaceutical composition comprising an antibacterial agent, a polymer, water and less than about 40% volatile solvent, in the preparation of a medicament for the treatment of a disease, disorder or condition of the skin.

In another embodiment, the invention relates to the use of a topical pharmaceutical composition comprising an antibacterial agent, a polymer, water and less than about 40% volatile solvent, in the treatment of a disease, disorder or condition of the skin.

DETAILED DESCRIPTION OF THE INVENTION

Figure 1:
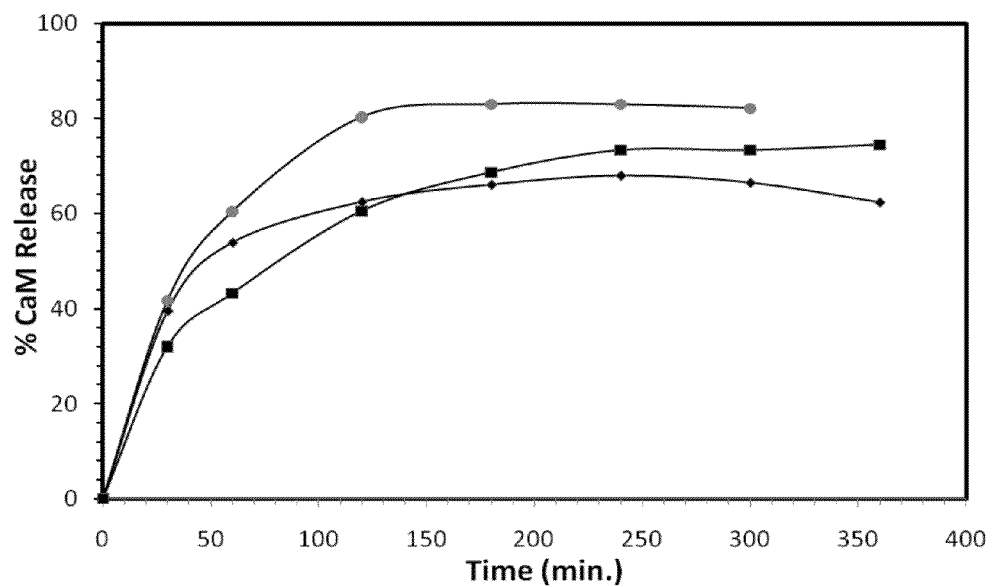
FIG. 1 illustrates modulation of the rate of release of calcium mupirocin where different variants of PVP/VA are used, i.e. PVP/VA 60:40 (●), PVP/VA 70:30 (♦) and PVP/VA 30:70 (■).

The present invention provides for a topical pharmaceutical composition comprising an antibacterial agent, a polymer, water and less than about 40% volatile solvent, and optionally additional dermatologically acceptable excipients.

Exemplary antibacterial agents include, but are not limited to, mupirocin, gentamicin, neomycin, streptomycin, cefpodoxime proxetil, clindamycin, lincomycin, erythromycin, bacitracin, gramicidin(s), vancomycin, doxycycline, minocycline, oxytetracycline, tetracycline, fosfomycin, fusidic acid, sulfacetamide, metronidazole, benzoyl peroxide and dapsone, pharmaceutically acceptable salts thereof, and mixtures thereof.

Suitably, the antibacterial agent is present in the composition in a therapeutically effective amount. In an embodiment, the antibacterial agent is present in an amount from about 0.1% to about 10% by weight.

In one embodiment, the antibacterial agent is selected from the group consisting of mupirocin, clindamycin, metronidazole and pharmaceutically acceptable salts thereof. In a particular embodiment, the antibacterial agent is mupirocin or a salt thereof. In an embodiment, the mupirocin or a salt thereof is calcium mupirocin. In one embodiment, the mupirocin or a salt thereof is sodium mupirocin. In one embodiment, the mupirocin or a salt thereof is calcium mupirocin. In another embodiment, the calcium mupirocin is present either as an amorphous or crystalline form. In another embodiment, the mupirocin or a salt thereof is mupirocin (the free acid). In yet another embodiment, the mupirocin or a salt thereof is a mixture of calcium mupirocin and mupirocin (the free acid). Suitably, the calcium mupirocin and mupirocin in such an embodiment are present in a ratio of about 1:3 to about 3:1, suitably about 1:1.

The benefit of combining calcium mupirocin and mupirocin (the free acid) in a single composition according to the present invention is that the respective forms of mupirocin will be released from the topical composition at different rates, so as to facilitate a combination of rapid release and more sustained release of the active agent. These differing release rates arise from the different hydrophilicity/hydrophobicity of calcium mupirocin and mupirocin (the free acid). The same would be present for sodium mupirocin and mupirocin (free acid), as well potentially as other salt forms of mupirocin with the free acid.

In an embodiment, the mupirocin or a salt thereof is present in an amount from about 0.1% to about 10% by weight. Suitably, the mupirocin or a salt thereof is present in an amount from about 1% to about 3% by weight, such as about 1%, 2% or 3% by weight, for example. In a particular embodiment, the mupirocin or a salt thereof is present in an amount of about 2% by weight.

In an alternative embodiment, the antibacterial agent is clindamycin or a salt thereof. Suitably, the clindamycin or a salt thereof is clindamycin phosphate or clindamycin hydrochloride. In an embodiment, the clindamycin or a salt thereof is clindamycin phosphate. In a further embodiment, the clindamycin or a salt thereof is present in an amount from about 0.5% to about 2% by weight, such as about 1% by weight.

In another embodiment, the antibacterial agent is metronidazole. Suitably, the metronidazole is present in an amount from about 0.1% to about 2% by weight. In a particular embodiment, the metronidazole is present in an amount of about 1% by weight.

Polymer

In an embodiment, the polymer present in the formulation is a copolymer.

Suitably, the copolymer is polyvinylpyrrolidone-vinyl acetate copolymer, also known as PVP/VA. In one embodiment, the ratio of PVP monomer to VA monomer in the PVP/VA copolymer is from about 30:70 to about 70:30. In another embodiment, the ratio of PVP monomer to VA monomer is about 30:70. In another embodiment, the ratio of PVP monomer to VA monomer is about 60:40. In yet another embodiment, the ratio of PVP monomer to VA monomer is about 70:30. While there are many suppliers of PVP/VA, many ratios are available from 70:30 to 20:80 are available under the tradename Luviskol, produced by BASF.

Hydrophobic polymers are either insoluble in low ethanolic formulations (≦20% ethanol) or precipitate out of the formulation due to interactions with the hydrophilic drug. Hydrophilic homopolymers (such as hydroxypropylcellulose (HPC)) form thermodynamically stable formulations, but tend to give rise to a burst release of a hydrophilic drug. A difference in drug release has been observed when the hydrophobicity of the copolymer PVP/VA is modified by changing the ratio of PVP (hydrophilic moiety) to VA (hydrophobic moiety) as will be further described herein in the Methods Section. A hydrophilic polymer (e.g. a carbomer and PVP/VA (60:40)) has also been shown to reduce the drug release of a lipophilic drug as compared to the hydrophilic drug.

In an embodiment, the polymer is present in the composition in an amount from about 1% to about 60% by weight. In one embodiment, the polymer is present in an amount from about 5% to about 30% by weight, such as about 10% by weight. In another embodiment, the polymer is present in an amount from about 30% to about 60% by weight, such as from about 45% to about 55% by weight, or about 50% by weight.

Water

In an embodiment, the composition comprises water in an amount from about 20% to about 85% by weight. In one embodiment, the composition comprises water in an amount from about 40% to about 85% by weight. In another embodiment the composition comprises from about 50% to about 70% by weight. In another embodiment, the composition comprises water in an amount from about 20% to about 40% by weight.

Volatile Solvent

In an embodiment, the volatile solvent is an organic solvent. The organic solvent is suitably selected from ethanol, propanol, iso-propanol, n-butyl alcohol, t-butyl alcohol, butoxy ethanol, acetone, ethyl acetate or butyl acetate, and mixtures thereof. In one embodiment the at least one volatile solvent present in the composition is ethanol.

In another embodiment, the volatile solvent is a mixture of at least two volatile solvents. Suitably the combination contains ethanol as the first solvent in combination with a second solvent. Suitably, the second solvent is propanol, iso-propanol, n-butyl alcohol, t-butyl alcohol, butoxy ethanol, acetone, ethyl acetate or butyl acetate. In an embodiment, the volatile solvent is a mixture of ethanol and iso-propanol. In another embodiment, the volatile solvent is a mixture of ethanol and ethyl acetate.

In an embodiment, the volatile solvent is present in an amount of less than about 40% by weight. In one embodiment, the volatile solvent is present in an amount from about 5% to about 30% by weight. In another embodiment, the volatile solvent is present in an amount from about 10% to about 25% by weight.

Suitably, the ratio of volatile solvent to water in the topical pharmaceutical composition is from about 1:1 to about 1:10. In one embodiment, the ratio of volatile solvent to water in the topical pharmaceutical composition is from about 1:1 to about 1:3. In an embodiment, the ratio of volatile solvent to water in the topical pharmaceutical composition is from about 1:1.25 to about 1:2. In another embodiment the ratio is about 1:1.65.

Second Pharmaceutically Active Agent

According to an embodiment, the topical pharmaceutical composition may comprise a second pharmaceutically acceptable active agent.

In one embodiment, the second pharmaceutically active agent is selected from the group consisting of a second antibacterial agent, a retinoid, a corticosteroid, an antifungal agent, a skin conditioning agent, a nutritional agent, and an antiseptic agent. Suitably, the second pharmaceutically active agent is present in an amount in the composition from about 0.001% to about 20% by weight, depending on the nature of the second active agent.

Exemplary antibacterial agents suitable for use as the second antibacterial agent include, but are not limited to, gentamicin, neomycin, streptomycin, cefpodoxime proxetil, clindamycin, lincomycin, erythromycin, bacitracin, gramicidin(s), vancomycin, doxycycline, minocycline, oxytetracycline, tetracycline, fosfomycin, fusidic acid, sulfacetamide, metronidazole, benzoyl peroxide and dapsone, salts thereof, and mixtures thereof. Suitably, the second antibacterial agent is present in an amount from about 0.1% to about 10% by weight.

Exemplary retinoids include, but are not limited to, tazarotene, tretinoin, isotretinoin, acitretin, etretinate, adapalene, bexarotene, alitretinoin, retinol, retinal, retinyl palmitate, retinyl acetate, retinyl propionate, retinyl linoleate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 6-(2-(4,4-dimethylthiochroman-6-yl)-ethynyl)pyridine-3-carbaldehyde, pharmaceutically acceptable salts thereof, and mixtures thereof. Suitably, the retinoid is present in an amount from about 0.01% to about 1% by weight.

In an embodiment, the retinoid is selected from the group consisting of tretinoin, tazarotene and adapalene. In one embodiment, the retinoid is tretinoin. In another embodiment, the retinoid is tazarotene. In yet another embodiment, the retinoid is adapalene.

Exemplary corticosteroids include, but are not limited to, alclometasone dipropionate, amcinonide, beclomethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, prednicarbate, salts thereof, and mixtures thereof. Suitably, the corticosteroid is present in an amount from about 0.01% to about 2% by weight.

Exemplary antifungal agents include, but are not limited to, those selected from the group consisting of echinocandins such as anidulafunin, caspofungin and micafungin; polyenes such as amphotericin B, candicidin, filipin, fungichromin, hachimycin, hamycin, lucensomycin, mepartricin, natamycin, nystatin, pecilocin, perimycin; allylamines such as butenafine, naftifine and terbinafine; imidazoles such as bifonazole, butoconazole, chlormidazole, cloconazole, clotrimazole, econazole, enilconazole, fenticonazole, flutrimazole, isoconazole, ketoconazole, lanoconazole, miconazole, neticonazole, omoconazole, oxiconazole nitrate, sertaconazole, sulconazole and tioconazole; thiocarbamates such as liranaftate, tolciclate, tolindate and tolnafate; triazoles such as albaconazole, pramiconazole, fluconazole, itraconazole, posaconazole, ravuconazole, saperconazole, terconazole and voriconazole; and other antifungal agents such as acrisorcin, amorolfine, biphenamine, bromosalicylchloranilide, buclosamide, calcium propionate, chlorphenesin, ciclopirox, cloxyquin, coparaffinate, exalamide, flucytosine, haloprogin, hexetidine, loflucarban, nifuratel, potassium iodide, propionic acid, pyrithione, salicylanilide, sodium propionate, sulbentine, tenonitrozole, triacetin, undecylenic acid, zinc propionate, griseofulvin, oligomycins, pyrroInitrin, siccanin, viridian, pharmaceutically acceptable salts thereof, and mixtures thereof. Suitably, the antifungal agent is present in an amount from about 0.1% to about 5% by weight.

Exemplary skin-conditioning agents include, but are not limited to, hydrocarbon oils and waxes, silicones, fatty acid derivatives, cholesterol, di- and tri-glycerides, vegetable oils, acetoglyceride esters, alkyl esters, alkenyl esters, lanolin, milk tri-glycerides, wax esters, beeswax, sterols, phospholipids, hyaluronic acid, pharmaceutically acceptable salts thereof, and mixtures thereof. In an embodiment, the skin-conditioning agent is hyaluronic acid or a salt thereof, such as sodium hyaluronate. Suitably, the skin conditioning agent is present in an amount from about 0.1% to about 20% by weight.

Exemplary nutritional agents include vitamins such as vitamins A, B, C, D, E and K and prodrugs thereof, essential amino acids, essential fats, antioxidants, pharmaceutically acceptable salts thereof, and mixtures thereof. Suitably, the nutritional agent is present in an amount from about 0.01% to about 2% by weight.

Exemplary antiseptics include, but are not limited to, hydrogen peroxide, chlorhexidine, cetrimide, povidone iodine, silver sulfadiazine, triclosan, pharmaceutically acceptable salts thereof, and mixtures thereof.

In another embodiment, the first antibacterial agent is mupirocin or a pharmaceutically acceptable salt thereof and the second pharmaceutically active agent is a second antibacterial agent. Suitably, the first antibacterial agent is mupirocin, sodium or calcium mupirocin or a mixture thereof. In one embodiment the first antibacterial agent is calcium mupirocin. In one embodiment, the second antibacterial agent is metronidazole. In another embodiment the first antibacterial agent is calcium mupirocin and the second antibacterial agent is metronidazole.

In another embodiment, the antibacterial agent is mupirocin or a pharmaceutically acceptable salt thereof and the second pharmaceutically active agent is a retinoid. Suitably, the antibacterial agent is mupirocin, sodium or calcium mupirocin or a mixture thereof. In one embodiment the antibacterial agent is calcium mupirocin. In one embodiment the retinoid is tretinoin. In another embodiment, retinoid is adapalene. In one embodiment the antibacterial agent is calcium mupirocin and the retinoid is tretinoin or adapalene.

In another embodiment, the antibacterial agent is mupirocin or a pharmaceutically acceptable salt thereof and the second pharmaceutically active agent is a corticosteroid. Suitably, the antibacterial agent is mupirocin, sodium or calcium mupirocin or a mixture thereof. In one embodiment the antibacterial agent is calcium mupirocin. In one embodiment, corticosteroid is clobetasol propionate. In another embodiment, corticosteroid is hydrocortisone or an ester thereof. In one embodiment the antibacterial agent is calcium mupirocin and the antibacterial agent is clobetasol propionate or hydrocortisone or an ester thereof.

In another embodiment, the antibacterial agent is mupirocin or a pharmaceutically acceptable salt thereof and the second pharmaceutically active agent is an antifungal agent. Suitably, the antibacterial agent is mupirocin, sodium or calcium mupirocin or a mixture thereof. In one embodiment the antibacterial agent is calcium mupirocin. In one embodiment, the antibacterial agent is calcium mupirocin and the antifungal agent is clotrimazole.

In another embodiment, the antibacterial agent is mupirocin or a pharmaceutically acceptable salt thereof and the second pharmaceutically active agent is a skin conditioning agent. Suitably, the mupirocin or pharmaceutically acceptable salt thereof is calcium mupirocin.

In another embodiment, the antibacterial agent is mupirocin or a pharmaceutically acceptable salt thereof and the second pharmaceutically active agent is an antiseptic agent. Suitably, the mupirocin or pharmaceutically acceptable salt thereof is calcium mupirocin.

Dermatologically Acceptable Excipients

In an embodiment, the present topical pharmaceutical compositions further comprise one or more dermatologically acceptable excipients.

Suitably, the excipient is selected from the group consisting of a co-solvent, a pH adjusting agent, a humectant, a film extender, a chelating agent, an antioxidant, a preservative, a gelling agent, a fragrance, a colorant, a penetration enhancer, or a combination or mixture thereof.

In one embodiment, the present compositions are formulated as a solution, gel, serum, aerosol spray or aerosol foam. Suitably, the composition is formulated as a solution. In another embodiment, the composition is formulated as a gel.

Co-Solvent

The topical pharmaceutical compositions may further comprise a co-solvent. The function of the co-solvent is to further solubilise (i.e. in conjunction with the volatile solvent) the active agent and/or the polymer in the composition.

Exemplary co-solvents include, but are not limited to, alcohols such as amyl alcohol, benzyl alcohol, cyclohexanedimethanol, diacetone alcohol, hexyl alcohol, tetrahydrofurfuryl alcohol; carboxylic acids such as acetic acid or multi carboxylic acid derivatives; diols such as 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, tripropylene glycol; and polyols such as polyethylene glycol, butanetriol, glycerol and 1,2,6-hexanetriol.

In one embodiment, the co-solvent is propylene glycol. In another embodiment, the co-solvent is hexylene glycol. In yet another embodiment, the co-solvent is a mixture of at least two co-solvents. In an embodiment, the co-solvent is a mixture of polyethylene glycol and propylene glycol.

In one embodiment, the co-solvent is present in the composition in an amount of from about 1% to about 30% by weight. In another embodiment, the co-solvent is present in an amount of from about 1% to about 10% by weight. In yet another embodiment, the co-solvent is present in an amount of from about 15% to about 25% by weight.

In an alternative embodiment, the topical pharmaceutical composition is devoid or substantially devoid of co-solvent. In one embodiment, the topical pharmaceutical composition is devoid of co-solvent. In another embodiment, the topical pharmaceutical composition is substantially devoid of co-solvent.

In another embodiment, the topical pharmaceutical composition comprises a volatile solvent in an amount from about 10% to about 25% by weight and is substantially devoid of a co-solvent. In yet another embodiment, the topical pharmaceutical composition comprises a volatile solvent in an amount from about 10% to about 25% by weight, and is devoid of co-solvent.

pH Adjusting Agent

The topical pharmaceutical compositions may further comprise a pH adjusting agent. In one embodiment, the pH adjusting agent is a base. Suitable bases include amines, bicarbonates, carbonates, and hydroxides such as alkali or alkaline earth metal hydroxides, as well as transition metal hydroxides. In an embodiment, the base is sodium hydroxide or potassium hydroxide.

In another embodiment, the pH adjusting agent is an acid, an acid salt, or mixtures thereof. Suitably, the acid is selected from the group consisting of lactic acid, acetic acid, maleic acid, succinic acid, citric acid, phosphoric acid, nitric acid, sulphuric acid and hydrochloric acid.

In yet another embodiment, the pH adjusting agent is a buffer. Suitably, the buffer is selected from the group consisting of citrate/citric acid, acetate/acetic acid, phosphate/phosphoric acid, propionate/propionic acid, lactate/lactic acid, carbonate/carbonic acid, ammonium/ammonia and edetate/edetic acid, or a combination or mixture thereof. In one embodiment, the pH adjusting agent is citrate/citric acid.

In one embodiment, the pH adjusting agent is present in an amount from about 0.01% to about 10% by weight. In another embodiment, the pH adjusting agent is present in an amount sufficient to adjust the pH of the composition to between about 4 to about 9. Suitably, the composition is adjusted to a pH between about 4 to about 6.5, or a pH between about 6.5 to about 9.

Humectant

The topical pharmaceutical compositions may further comprise a humectant.

Exemplary humectants include, but are not limited to, glycerol, sorbitol, maltitol, polydextrose, triacetin, propylene glycol, polyethylene glycol (PEG) esters including PEG-20 stearate, PEG-40 stearate, PEG-150 stearate, PEG-150 distearate and PEG-100 stearate, alkoxylated alcohols including laureth-12, ceteareth-20, laureth-23, glycereth-7, glycereth-12, glycereth-26, PEG-4, PEG-6, PEG-8, PEG-12, PEG-32, PEG-75, PEG-150, or a combination or mixture thereof. In an embodiment, the humectant is glycerol.

In one embodiment, the present compositions comprise about 0.1% to about 10% by weight of a humectant. In another embodiment, the compositions comprise about 0.5% to about 5% by weight of a humectant.

Film Extenders

The present topical pharmaceutical compositions may further comprise a film extender. Exemplary film extenders include, but are not limited to, calcium carbonate, calcium phosphate, calcium stearate, magnesium stearate, zinc stearate, calcium sulfate, colloidal silicon dioxide, kaolin, magnesium carbonate, magnesium silicate, sodium stearyl fumarate, talc, titanium dioxide, zinc oxide, or a combination or mixture thereof.

Suitably, the film extender is present in an amount from about 0.1% to about 2% by weight.

Chelating Agents

The present topical pharmaceutical compositions may further comprise a chelating agent. Exemplary chelating agents include, but are not limited to, citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), ethylene diamine tetraacetic acid (EDTA), dihydroxyethylglycine (DEG), diethylene triamine pentaacetic acid (DPTA), nitrilotriacetic acid (NTA), N-(hydroxyethyl)-ethylenetriaminetriacetic acid (HEDTA), aminocarboxylates, dimercaperol (BAL), larixinic acid (maltol), unidentate ligands (fluoride and cyanide ions), diphenylthiocarbazone, o-phenanthroline, barium diphenylamine sulfonate, sodium glucoheptonate, 8-hydroxyquinoline, olefin complexes (such as dicyclopentadienyl iron), porphyrins, phosphonates, or a combination or mixture thereof.

In one embodiment, the chelating agent is EDTA.

Suitably, the chelating agent is present in an amount from about 0.1% to about 1% by weight.

Antioxidants

The present topical pharmaceutical compositions may further comprise an antioxidant. Exemplary antioxidants include, but are not limited to, butylated hydroxytoluene (BHT), butylated hydroxyanisole, tocopherol, propyl gallate, vitamin E TPGS, or a combination or mixture thereof.

Suitably, the present compositions comprise an antioxidant in an amount from about 0.001% to about 1% by weight.

Preservatives

The present topical pharmaceutical compositions may further comprise a preservative. Exemplary preservatives include, but are not limited to, benzyl alcohol, diazolidinyl urea, methyl paraben, ethyl paraben, propyl paraben, butyl paraben, phenoxyethanol, sorbic acid, benzoic acid, salts thereof, or a combination or mixture thereof. In one embodiment, the preservative is benzyl alcohol. In another embodiment, the preservative is phenoxyethanol.

Suitably, the present compositions comprise a preservative in an amount from about 0.01% to about 2% by weight.

Gelling Agent

The present topical pharmaceutical compositions may further comprise a gelling agent. Exemplary gelling agents include, but are not limited to, agar, alginate, arabinoxylan, carrageenan, carboxymethylcellulose, hydroxypropyl methylcellulose, cellulose, curdlan, gelatin, gellan, β-glucan, tragacanth gum, guar gum, gum arabic, locust bean gum, pectin, starch, a carbomer, acrylate copolymers, silica, xanthan gum, salts thereof, or a combination or mixture thereof.

In one embodiment, the gelling agent is xanthan gum. In another embodiment, the gelling agent is a carbomer. In another embodiment, the gelling agent is a mixture of at least two gelling agents.

Suitably, the gelling agent is present in the composition in an amount from about 0.1% to about 2% by weight.

In one embodiment, the invention provides a topical pharmaceutical composition comprising:
(a) calcium mupirocin,
(b) a polymer in an amount from about 30% to about 60% by weight,
(c) water in an amount from about 20% to about 40% by weight, and
(d) a volatile solvent in an amount from about 10% to about 25% by weight.

In another embodiment, the invention provides a topical pharmaceutical composition comprising:
(a) calcium mupirocin,
(b) a polymer in an amount from about 30% to about 60% by weight,
(c) water in an amount from about 20% to about 40% by weight,
(d) a volatile solvent in an amount from about 10% to about 25% by weight, and
(e) a gelling agent.

In yet another embodiment, the invention provides a topical pharmaceutical composition comprising:
(a) calcium mupirocin,
(b) a polymer in an amount from about 30% to about 60% by weight,
(c) water in an amount from about 20% to about 40% by weight, and
(d) a volatile solvent in an amount from about 10% to about 25% by weight, and
wherein the composition is devoid or substantially devoid of co-solvent.

In another embodiment, the invention provides a topical pharmaceutical composition comprising:
(a) calcium mupirocin,
(b) a polymer in an amount from about 30% to about 60% by weight,
(c) water in an amount from about 20% to about 40% by weight,
(d) a volatile solvent in an amount from about 10% to about 25% by weight, and
(e) a gelling agent, and
wherein the composition is devoid or substantially devoid of co-solvent.

Suitably, the polymer in any of the above 4 formulations is PVP/VA. In one embodiment, the ratio of PVP monomer to VA monomer in the PVP/VA is from about 30:70 to about 70:30. In a particular embodiment, the ratio of PVP monomer to VA monomer is about 30:70. In another embodiment, the ratio of PVP monomer to VA monomer is about 60:40. In yet another embodiment, the ratio of PVP monomer to VA monomer is about 70:30.

Suitably, the calcium mupirocin is present in an amount from about 1% to about 3% by weight. In one embodiment, the calcium mupirocin is present in an amount from about 2% by weight.

In another embodiment, the topical pharmaceutical composition is devoid or substantially devoid of a lipid. In one embodiment, the pharmaceutical composition is devoid of a lipid. In a further embodiment, the pharmaceutical composition is substantially devoid of a lipid.

Methods of Treatment

According to an embodiment, the invention provides a method of treating a disease, disorder or condition of the skin, the method comprising administering to a subject in need thereof, a topical pharmaceutical composition comprising an antibacterial agent, a polymer, water and less than about 40% volatile solvent.

In a particular embodiment, the disease, disorder or condition of the skin is caused by a bacterial infection.

Exemplary bacterial infections include, but are not limited to, infections caused by Gram-positive and Gram-negative bacteria and mycoplasmas, including for example, *Staphylococcus aureus, Staphylococcus epidermidis, Staphylococcus haemolyticus, Staphylococcus hominis, Staphylococcus sapropphyticus, Streptococcus pyogenes, Streptococcus agalactiae, Streptococcus pneumoniae, Streptococcus mutans, Streptococcus sanguis, Streptococcus faecium, Streptococcus faecalis, Corynebacterium hofmannii, Bacillus subtilis, Neisseria meningitides, Neisseria gonorrhoeae, Haemophilus influenzae, Pasteurella multocida, Branhamella catarrhalis, Proteus vulgaris, Propionibacterium acnes, Enterobacter cloacae, Peptostreptococcus anaerobius, Clostridium sporogenes, Clostridium difficile, Moraxella catarrhalis, Mycoplasma pneumoniae* and *Mycoplasma gallisepticum*.

Suitably, the bacterial infection is an infection caused by *Staphylococcus aureus*.

In an embodiment, the disease, disorder or condition of the skin caused by a bacterial infection is acne, impetigo, superficially infected dermatoses, wounds which have become infected, rosacea or folliculitis.

In one embodiment, the disease, disorder or condition of the skin is acne. In another embodiment, the disease, disorder or condition of the skin is impetigo.

In a further embodiment, the present compositions may be used as part of a regimen for the treatment or prevention of a disease, disorder or condition of the skin. In particular, the present compositions may be used in combination with a separate pharmaceutical dosage form. According to an embodiment, the separate pharmaceutical dosage form is an oral preparation. In one embodiment, the oral preparation is a capsule or tablet comprising an antibacterial agent.

Definitions

The phrases an "effective amount", "an amount effective to" or a "therapeutically effective amount" are used herein to refer to an amount of the composition sufficient to have a therapeutic effect upon administration. Effective amounts will vary with the particular condition or conditions being treated, the severity of the condition, the duration of the treatment, and the specific components of the composition.

The terms "administering" and "administration" are used herein to mean any method which in sound medical practice delivers the composition to a subject in such a manner as to provide the desired therapeutic effect.

The terms "treatment" or "treating" of a skin disease, disorder or condition encompasses alleviation of at least one symptom thereof, a reduction in the severity thereof, or the delay, prevention or inhibition of the progression thereof. Treatment need not mean that the disorder is totally cured. A useful composition herein need only to reduce the severity of the disorder, reduce the severity of symptoms associated therewith, provide improvement to a patient's quality of life, or delay, prevent or inhibit the onset of the disorder.

The term "lipid" is a generic term to describe fats and oils, such as fatty acids, esters of fatty acids, esters of glycerin, fatty alcohols, waxes, unsaponifiables, sterols, siloxanes, silanes, lanolin, hydrocarbons, glyceryl esters, essential oils, vegetable oils, mineral oils, animal oils and edible oils.

The term "salt thereof" refers to salts that are pharmaceutically acceptable. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion or an aluminium ion; or (ii) protonates an organic base such as, for example, ethanolamine, diethanolamine, triethanolamine, tromethamine and N-methylglucamine.

Any concentration range, percentage range or ratio range recited herein is to be understood to include concentrations, percentages or ratios of any integer within that range and fractions thereof, such as one tenth and one hundredth of an integer, unless otherwise indicated.

It should be understood that the terms "a" and "an" as used herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Throughout the application, descriptions of various embodiments use "comprising" language, however in some specific instances, an embodiment can alternatively be described using the language "consisting essentially of" or "consisting of".

All numbers expressing quantities, percentages or proportions, and other numerical values used in the specification and claims, are to be understood as being modified in all instances by the term "about."

"Substantially devoid" of a specified component refers to a composition with less than about 1% by weight of the specified component. "Devoid" of a specified component refers to a composition where the specified component is absent.

Other terms used herein are intended to be defined by their well known meanings in the art.

EXAMPLES

The invention will now be described by reference to the following examples which are merely illustrative and are not to be construed as a limitation of the scope of the present invention.

The following compositions of Examples 1 and 2 may be prepared by the methods of preparation as set forth below in Example 4.

Example 1

Calcium Mupirocin Polymeric Composition

| Item | Ingredient | % by weight |
| --- | --- | --- |
| 1 | PVP/VA 30:70 | 10 |
| 2 | Ethanol | 10 |
| 3 | Water | 59.5 |
| 4 | Hexylene glycol | 20 |
| 5 | Calcium mupirocin | 0.5 |
| | Total | 100 |

Example 2

Mupirocin Polymeric Composition

| Item | Ingredient | % by weight |
| --- | --- | --- |
| 1 | PVP/VA 30:70 | 10 |
| 2 | Ethanol | 10 |
| 3 | Water | 55.7 |
| 4 | Hexylene glycol | 23.8 |
| 5 | Mupirocin | 0.5 |
| | Total | 100 |

Example 3

Additional Polymeric Compositions

The following placebo compositions were also prepared. Each composition was a clear solution. The mupirocin calcium or mupirocin may be added to the placebo composition to form the final composition. A number of the compositions prepared were devoid of co-solvent (i.e. devoid of hexylene glycol), but yet were still a clear solution.

| Item | Ingredient | % | % | % | % | % | % | % | % | % | % |
| --- | --- | --- | --- | --- | --- | --- | --- | --- | --- | --- | --- |
| 1 | PVP/VA 30:70 | 11.9 | 12 | 4 | 10.2 | 10.3 | 3.2 | 10.7 | 20.9 | 49.1 | 49.8 |
| 2 | Ethanol | 23.4 | 24.5 | 23 | 21 | 20.7 | 23.8 | 4.7 | 5.5 | 17.9 | 18.9 |

-continued

| Item | Ingredient | % | % | % | % | % | % | % | % | % | % |
|------|------------|------|------|----|------|------|----|------|------|------|------|
| 3 | Water | 64.7 | 63.5 | 73 | 66.2 | 66.9 | 73 | 65.6 | 56.3 | 31.1 | 31.3 |
| 4 | Hexylene glycol | 0 | 0 | 0 | 2.6 | 2.1 | 0 | 19 | 17.3 | 1.9 | 0 |
|   | Total | 100 | 100 | 100 | 100 | 100 | 100 | 100 | 100 | 100 | 100 |

Example 4

Methods of Preparation

Preparation of Calcium Mupirocin and Mupirocin Compositions Using PVP/VA (30:70)

PVP/VA (30:70) is available as a 50% mixture in ethanol (Luviskol® VA 37E, BASF). PVP/VA (30:70) as an ethanol solution was added to water and a turbid solution formed. Hexylene glycol was subsequently added to form a transparent solution. Calcium mupirocin or mupirocin was added and dissolved by vigorously shaking and rotating the preparation for 60 minutes (in accordance with Examples 1 and 2 respectively).

Preparation of a Calcium Mupirocin Composition Using PVP/VA (60:40 and 70:30)

Calcium mupirocin was dissolved in water followed by addition of an ethanolic solution of PVP/VA (70:30) (Luviskol® VA 73E, BASF). A transparent solution resulted. Hexylene glycol was not required.

Similarly, calcium mupirocin was dissolved in water, followed by the addition of ethanol, and then PVP/VA (60:40) powder (Plasdon S630, ISP Corp.) was added. A transparent solution resulted. Hexylene glycol was not required.

Preparation of Placebos Using PVP/VA (30:70)

An ethanolic solution of PVP/VA (30:70) was applied to a polypropylene sheet and dried in an oven at 800° C. until the ethanol had evaporated so as to afford a dried power. The dried PVP/VA powder was dissolved in ethanol to form a transparent solution, followed by addition of water. Addition of water was carefully monitored to observe the transformation from a transparent solution into a turbid mixture. Where a turbid mixture resulted, hexylene glycol was added dropwise until a transparent solution was obtained. The use of PVP/VA (30:70) powder rather than an ethanolic solution of the polymer, afforded a number of compositions where the polymer could be solubilised in low levels of ethanol, yet be devoid of hexylene glycol.

Example 5

Polymeric Compositions

The following compositions (Examples 5a-5f) further exemplify the present invention.

Example 5a

Co-Solvent Free/Low Ethanol Calcium Mupirocin Polymeric Solution

| Item | Ingredient | % by weight |
|------|------------|-------------|
| 1 | PVP/VA 30:70 | 48 |
| 2 | Ethanol | 19 |
| 3 | Water | 31 |
| 4 | Calcium mupirocin | 2 |
|   | Total | 100 |

Example 5b

Co-Solvent Free/Low Ethanol Calcium Mupirocin Polymeric Gel

| Item | Ingredient | % by weight |
|------|------------|-------------|
| 1 | PVP/VA 30:70 | 47 |
| 2 | Ethanol | 19 |
| 3 | Water | 31 |
| 4 | Xanthan gum | 1 |
| 5 | Calcium mupirocin | 2 |
|   | Total | 100 |

Example 5c

Co-Solvent Free/Low Ethanol Clindamycin Phosphate Polymeric Gel

| Item | Ingredient | % by weight |
|------|------------|-------------|
| 1 | PVP/VA 30:70 | 25 |
| 2 | Ethanol | 10 |
| 3 | Water | 62.75 |
| 4 | Xanthan gum | 1 |
| 5 | Clindamycin phosphate | 1.25 |
|   | Total | 100 |

Example 5d

Co-Solvent Free/Low Ethanol Metronidazole Polymeric Gel

| Item | Ingredient | % by weight |
|------|------------|-------------|
| 1 | PVP/VA 30:70 | 25 |
| 2 | Ethanol | 10 |
| 3 | Water | 63 |

| Item | Ingredient | % by weight |
|---|---|---|
| 4 | Xanthan gum | 1 |
| 5 | Metronidazole | 1 |
|  | Total | 100 |

Example 5e

Calcium Mupirocin in Combination with (1) Mupirocin, (2) Clotrimazole, (3) Hyaluronic Acid and (4) Clobetasol Propionate

| Ingredient | (1) % by weight | (2) % by weight | (3) % by weight | (4) % by weight |
|---|---|---|---|---|
| PVP/VA 30:70 | 10 | 50 | 50 | 50 |
| Ethanol | 10 | 19 | 19 | 19 |
| Water | 58 | 28 | 27 | 28.95 |
| Hexylene glycol | 20 | 0 | 0 | 0 |
| Actives | 1% mupirocin Ca 1% mupirocin | 2% mupirocin Ca 1% clotrimazole | 2% mupirocin Ca 2% hyaluronic acid | 2% mupirocin Ca 0.05% clobetasol propionate |
| Total | 100 | 100 | 100 | 100 |

Example 5f

Calcium Mupirocin in Combination with (5) Tretinoin, (6) Hydrocortisone, (7) Adapalene and (8) Metronidazole

| Ingredient | (5) % by weight | (6) % by weight | (7) % by weight | (8) % by weight |
|---|---|---|---|---|
| PVP/VA 30:70 | 50 | 50 | 50 | 50 |
| Ethanol | 19 | 19 | 19 | 19 |
| Water | 28.975 | 28 | 28.9 | 28.5 |
| Hexylene glycol | 0 | 0 | 0 | 0 |
| Actives | 2% mupirocin Ca 0.025% tretinoin | 2% mupirocin Ca 1% hydrocortisone | 2% mupirocin Ca 0.1% adapalene | 2% mupirocin Ca 0.5% metronidazole |
| Total | 100 | 100 | 100 |  |

Example 6

Drug Release

The following formulations were also prepared and used to assess drug release from the compositions of the present invention.

| Ingredient | % by weight | % by weight | % by weight |
|---|---|---|---|
| PVP/VA | (70:30) 10 | (60:40) 10 | (30:70) 10 |
| Ethanol | 10 | 10 | 10 |
| Water | 79.5 | 78 | 59.5 |

| Ingredient | % by weight | % by weight | % by weight |
|---|---|---|---|
| Hexylene glycol | 0 | 0 | 20 |
| Calcium mupirocin | 0.5 | 2 | 0.5 |
| Total | 100 | 100 | 100 |

Methodology:

Franz Cell Drug Release Studies

In vitro drug release experiments were carried out using a Franz cell methodology (Fan et al. (2004) J. Contr. Rel. 98, 355-365).

A Franz cell apparatus was used (Permegear, USA) with 12 mL 0.01 M PBS solution, pH 7.4 (Aldrich) in the Franz cell receptor compartment and the donor compartment. Two hydrophilic Durapore™ polyvinylidene fluoride membranes (Millipore) were placed between the receptor and donor compartments (25 mm diameter, 0.1 μm pore size with 70% porosity, 125 μm thickness). The temperature of the Franz cells was optimized and maintained at 30° C.

About 30-50 mg of each formulation was placed on the membranes from the donor compartment. 200 μL aliquots of the receptor phase were drawn at certain time intervals and subjected to HPLC analysis for drug content. Each aliquot was replaced by an equivalent amount of PBS solution.

HPLC Analysis

Methanol:$H_2O$ (50:50) was used as the diluent for the HPLC sample preparations. A reversed phase HPLC analytical method was used, with an Apollo $C_{18}$ column (150×4.6 mm, 5 μm), Photodiode array detector (210-300 nm range, detection at 223 nm), with isocratic elution at 1.5 mL/min and a mobile phase containing 55% methanol and 45% 0.1 M ammonium acetate buffer (pH 5.7). The retention time of calcium mupirocin was about 6 minutes and the total run time was 10 minutes. The error of analysis in the HPLC analyses was found to be 2-5%. Standard deviation (SD) and % relative standard deviation (% RSD) were found to be in the range of 1-7% and about 20%, respectively.

Results and Discussion

In an attempt to prepare a homogeneous topical composition comprising calcium mupirocin where the rate of release of the active is modulated, a number of polymers (Eudragit E100, Eudragit S100, Eudragit NE30D and Eudragit RLPO) were explored, but these polymers generally precipitated from the composition.

Desirably, PVP/VA was shown to be able to modulate release of the active agent, but remain solubilized in the composition. In particular, PVP/VA with varying ratios of PVP:VA monomers were explored, namely 70:30, 60:40 and 30:70. It was observed that PVP/VA 60:40 and 70:30 were soluble in compositions comprising 10% ethanol. However PVP/VA 30:70 was not soluble and required the addition of 20% hexylene glycol to solubilize the copolymer. It was later demonstrated, however, that a composition comprising PVP/VA 30:70 but devoid of hexylene glycol could be prepared by using PVP/VA 30:70 polymer powder, rather than as an ethanolic solution of the polymer. The PVP/VA 30:70 as a powder, rather than an ethanolic solution, afforded greater control over the relative concentrations of polymer, ethanol and water present in the composition.

Modulation in the rate of release of calcium mupirocin is illustrated in FIG. 1. This figure shows that for the composition comprising PVP:VA 30:70, calcium mupirocin release reached equilibrium after 4 hours. This compares to only 2 hours for the PVP:VA formulations having 60:40 and 70:30 ratios. This demonstrates a more gradual release of active agent where the ratio of the hydrophobic monomer (VA) is greater than the ratio of the hydrophilic monomer (PVP), i.e. as is the case for PCP/VA 30:70.

Figure 2:
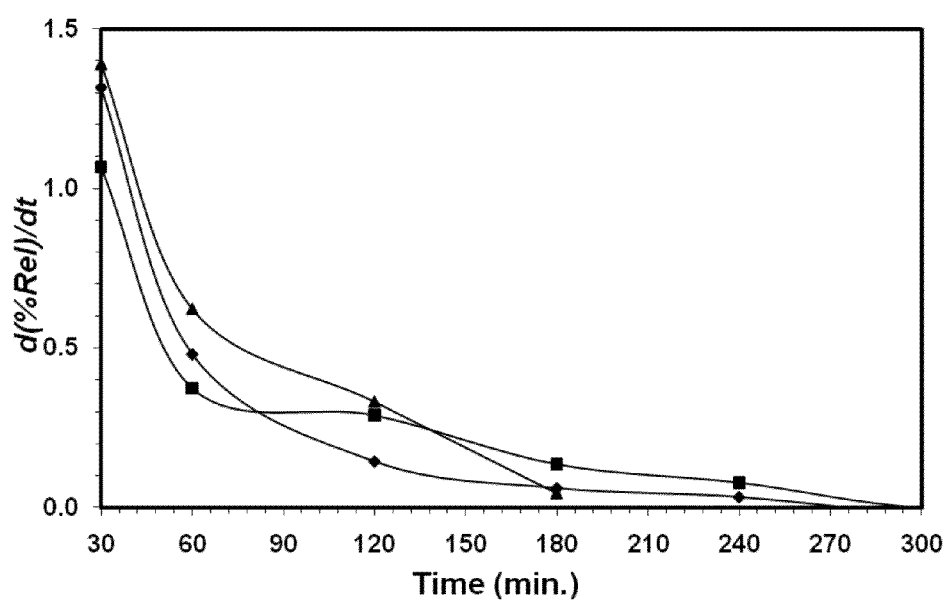
FIG. 2 illustrates modulation of the rate of release of calcium mupirocin (first order derivative) where different variants of PVP/VA are used, i.e. PVP/VA 60:40 (●), PVP/VA 70:30 (♦) and PVP/VA 30:70 (■).

FIG. 2 illustrates the first order derivative of the release data. These data show a clear difference in the release profile of PVP/VA 30:70 copolymer (on the one hand) and PVP:VA 60:40 and PVP:VA 70:30.

Figure 3:
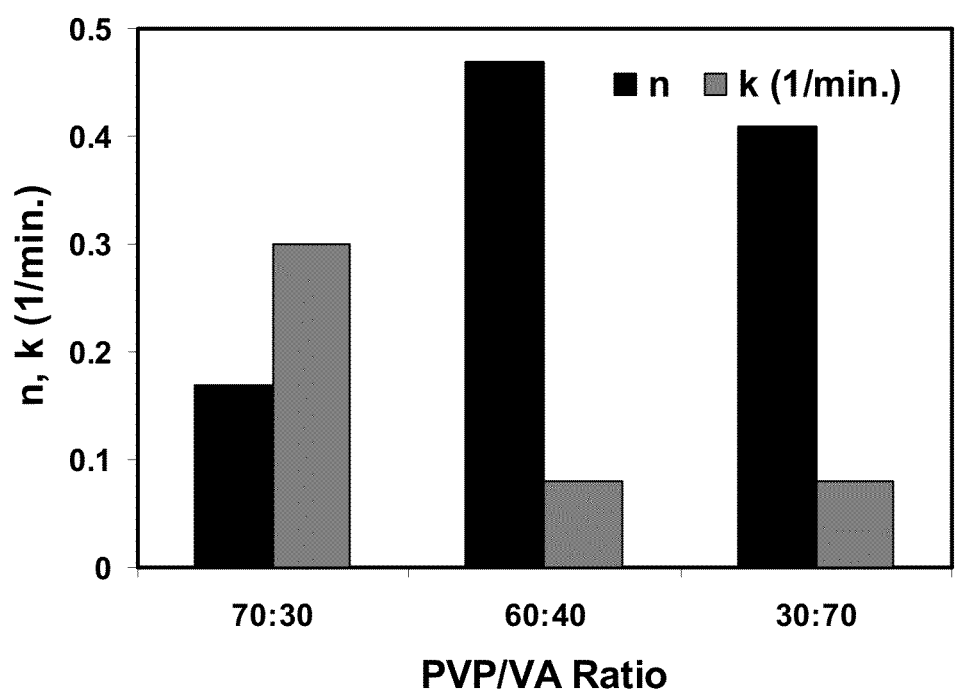
FIG. 3 illustrates the rate constant (k) and release exponent (n) in connection with release of calcium mupirocin from compositions comprising different variants of PVP/VA, i.e. PVP/VA 60:40, PVP/VA 70:30 and PVP/VA 30:70.

FIG. 3 illustrates that as the PVP/VA ratio changes from 70:30 to 60:40 to 30:70 (increasing hydrophobicity), wherein the release exponent (n) increases from 0.17 for PVP:VA 70:30 to 0.47 for PVP:VA (60:40) and 0.41 for PVP:VA (30:70). Furthermore, the rate constant (k) is reduced from 0.3 $min^{-1}$ (for PVP:VA 70:30) to 0.08 $min^{-1}$ (for both PVP:VA 60:40 and PVP:VA 30:70).

Thus, the n and k values are affected by changes in the hydrophobicity of the respective PVP/VA copolymers.

Example 7

Rub Resistance and Water Resistance

The following placebo formulations were to assess the water- and rub-resistance of the compositions of the present invention.

| Ingredient | % by weight | % by weight | % by weight | % by weight |
|---|---|---|---|---|
| Polymer (PVP/VA) | 10 | 11.9 | 12 | 11 |
| Ethanol | 10 | 23.4 | 24.5 | 20 |
| Water | 60 | 64.7 | 63.5 | 69 |
| Hexylene glycol | 20 | 0 | 0 | 0 |
| Total | 100 | 100 | 100 | 100 |

Methodology

Rub Resistance Studies

Around 20 mg of each formulation was spread evenly on separate glass slides. The slides were dried at 45° C. for 3 hours. Each film was subjected to abrasion with a 100 gm standard weight covered with a lint free tissue (Kimwipes™, Kimberley-Clark). In particular, the 100 gm standard weight covered with a lint free tissue was slowly oscillated 20 times back and forth over each dried film. The weight of the glass slides with the dried films before and after the abrasion was measured to evaluate the rub-resistance of each film.

Water Resistance Studies

Transpore™ medical tape (3M) was affixed to glass slides. Around 200 mg of each formulation was spread evenly on the medical tape. The slides were then dried at 45° C. for 3 hours. The weight of each dried plate was noted. The dried plates were subsequently immersed in water at 45° C. for 30 minutes. The plates were removed from the water and dried. Again, the weight of each slide was noted.

The difference in the weight of each slide (i.e. before and after being immersed in water) was calculated and represented the wash resistance of the polymeric films.

Results and Discussion

Figure 4:
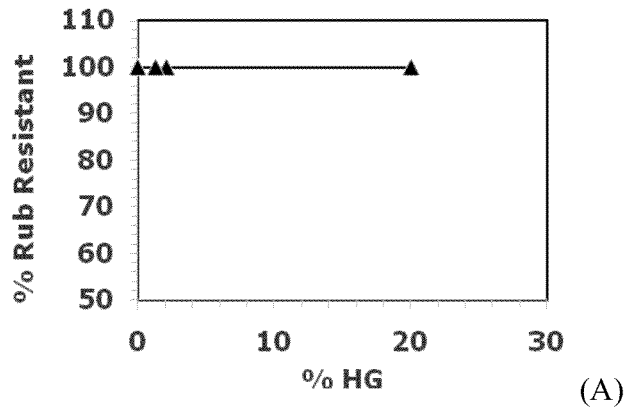
FIGS. 4a-4c illustrates the rub and water resistance of the compositions of the invention.
Figure 4:
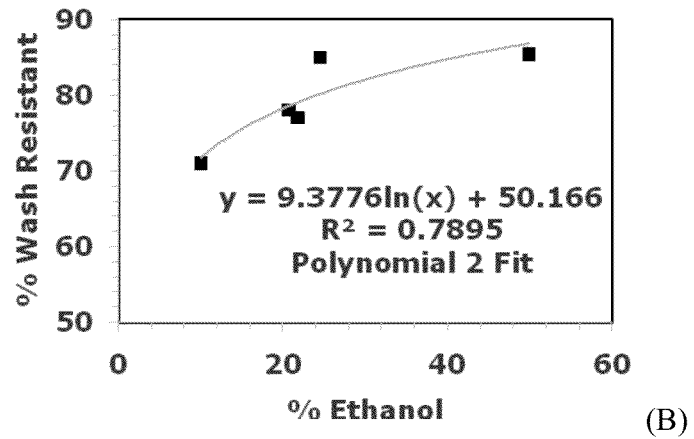
Figure 4:
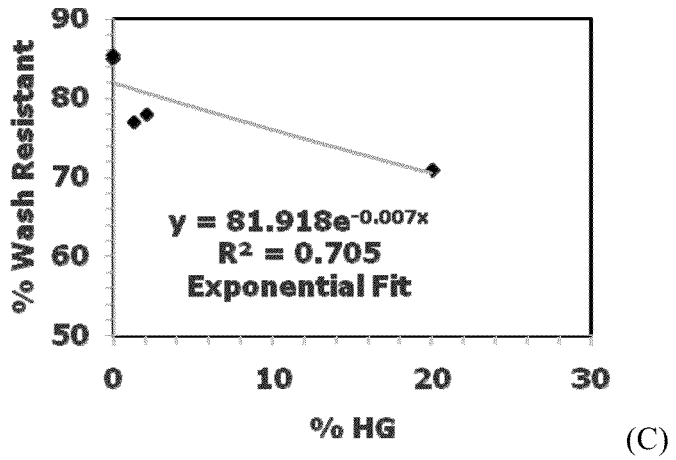

FIG. 4(a) illustrates that the addition of hexylene glycol does not impact the rub resistance of the compositions.

FIG. 4(b) illustrates that good wash resistance may be obtained with compositions comprising low amounts of ethanol e.g. about 20%.

FIG. 4(c) illustrates that the addition of hexylene glycol negatively impacts the wash resistance of the compositions of the invention.

These data demonstrate that a composition with about 20% ethanol, and free of hexylene glycol, will have both adequate water and rub resistance. It was also observed that the compositions without hexylene glycol dried down more rapidly, and result in a cosmetically elegant film (i.e. without the stickiness or tackiness associated with hexylene glycol).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A topical pharmaceutical composition comprising:
   (a) calcium mupirocin,
   (b) a polyvinvylpyrrolidone-vinyl acetate (PVP/VA) co-polymer in an amount from about 30% to about 60% by weight,
   (c) water in an amount from about 20% to about 40% by weight, and
   (d) a volatile solvent in an amount from about 10% to about 25% by weight; and optionally a gelling agent, and other dermatologically acceptable excipients thereof.

2. The composition according to claim 1 wherein the volatile solvent is a mixture of at least two volatile solvents, and wherein the first volatile solvent is ethanol.

3. The composition according to claim 1 wherein the ratio of PVP monomer to VA monomer in the PVP/VA copolymer is from about 30:70 to about 70:30.

4. The composition according to claim 1 wherein the PVP/VA copolymer is solublized in the composition.

5. The composition according to claim 1 wherein the volatile solvent is selected from ethanol, propanol, iso-propanol, n-butyl alcohol, t-butyl alcohol, butoxy ethanol, acetone, ethyl acetate or butyl acetate.

6. The composition according to claim 1 wherein the dermatologically acceptable excipients are selected from the group consisting of a co-solvent, a pH adjusting agent, a humectant, a film extender, a chelating agent, an antioxidant, a preservative, a fragrance, a colorant, a penetration enhancer, and a combination or mixture thereof.

7. The composition according to claim 1 wherein the gelling agent is xanthan gum.

8. The composition according to claim 1 wherein the topical pharmaceutical composition further comprises a second pharmaceutically acceptable active agent.

9. The composition according to claim 1 wherein the volatile solvent is ethanol.

10. The composition according to claim 1 wherein the calcium mupirocin is present in an amount from about 0.1% to about 10% by weight.

11. The composition according to claim 2 wherein the volatile solvent is a mixture of ethanol and iso-propanol.

12. The composition according to claim 2 wherein the volatile solvent is a mixture of ethanol and ethyl acetate.

13. The composition according to claim 3 wherein ratio of PVP monomer to VA monomer in the PVP/VA copolymer is about 30:70 and wherein the composition is free of hexylene glycol.

14. The composition according to claim 3 wherein the ratio of PVP monomer to VA monomer in the PVP/VA is about 60:40.

15. The composition according to claim 5 wherein the volatile solvent is ethanol.

16. The composition according to claim 5 wherein the dermatologically acceptable excipients are selected from the group consisting of a co-solvent, a pH adjusting agent, a humectant, a film extender, a chelating agent, an antioxidant, a preservative, a fragrance, a colorant, a penetration enhancer, and a combination or mixture thereof.

17. The composition according to claim 6 which composition is substantially devoid or devoid of a co-solvent.

18. The composition according to claim 6 wherein the co-solvent is selected from an alcohol, a carboxylic acid, a diol, a polyol or a combination or mixture thereof, present in an amount from about 1% to about 30% by weight.

19. The composition according to claim 6 wherein the co-solvent is a mixture of polyethylene glycol and propylene glycol.

20. The composition according to claim 8 wherein the second pharmaceutically acceptable active agent is selected from the group consisting of a second antibacterial agent, a retinoid, a corticosteroid, an antifungal agent, a skin conditioning agent, a nutritional agent, or an antiseptic agent.

21. The composition according to claim 8 wherein the second pharmaceutically acceptable active agent is mupirocin, clotrimazole, clobetasol propionate or hyaluronic acid.

22. The composition according to claim 10 wherein the calcium mupirocin is present in an amount from about 1% to about 3% by weight.

23. The composition according to claim 16 wherein the gelling agent is xanthan gum.

24. The composition according to claim 16 wherein the at least one co-solvent is selected from an alcohol, a carboxylic acid, a diol, a polyol or a combination or mixture thereof, present in an amount from about 1% to about 30% by weight.

25. The composition according to claim 18 wherein the alcohol is selected from amyl alcohol, benzyl alcohol, cyclohexanedimethanol, diacetone alcohol, hexyl alcohol, or tetrahydrofurfuryl alcohol; and the diol is selected from 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, or tripropylene glycol; and the polyol is selected from polyethylene glycol, butanetriol, glycerol or 1,2,6-hexanetriol.

26. The composition according to claim 18 wherein the co solvent is propylene glycol.

27. The composition according to claim 22 wherein the calcium mupirocin is present in an amount of about 2% by weight.

28. The composition according to claim 24 wherein the alcohol is selected from amyl alcohol, benzyl alcohol, cyclohexanedimethanol, diacetone alcohol, hexyl alcohol, or tetrahydrofurfuryl alcohol; and the diol is selected from 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, or tripropylene glycol; and the polyol is selected from polyethylene glycol, butanetriol, glycerol or 1,2,6-hexanetriol.

29. The composition according to claim 25 wherein the gelling agent is xanthan gum.

* * * * *